(12) United States Patent  
Saito et al.

(10) Patent No.: US 7,880,862 B2
(45) Date of Patent: Feb. 1, 2011

(54) EXPOSURE APPARATUS AND DEVICE FABRICATION METHOD

(75) Inventors: Nobuyuki Saito, Utsunomiya (JP); Haruna Kawashima, Haga-gun (JP)

(73) Assignee: Canon Kabushiki Kaisha (JP)

( * ) Notice: Subject to any disclaimer, the term of this patent is extended or adjusted under 35 U.S.C. 154(b) by 513 days.

(21) Appl. No.: 11/959,622

(22) Filed: Dec. 19, 2007

(65) Prior Publication Data

US 2008/0151251 A1    Jun. 26, 2008

(30) Foreign Application Priority Data

Dec. 21, 2006   (JP)   ............... 2006-344694

(51) Int. Cl.
 *G03B 27/74*   (2006.01)
 *G03B 27/54*   (2006.01)

(52) U.S. Cl. .......................................... 355/68; 355/67

(58) Field of Classification Search .................. 355/53, 355/67–71; 356/512, 399–401
See application file for complete search history.

(56) References Cited

U.S. PATENT DOCUMENTS

2006/0170891 A1*   8/2006   Nishinaga et al. ............. 355/53

FOREIGN PATENT DOCUMENTS

| JP | 2005-175034 | 6/2005 |
| JP | 2005-223275 | 8/2005 |
| JP | 2005-268744 | 9/2005 |

* cited by examiner

*Primary Examiner*—Hung Henry Nguyen
(74) *Attorney, Agent, or Firm*—Rossi, Kimms & McDowell LLP

(57) ABSTRACT

An exposure apparatus comprising a projection optical system configured to project a pattern image of an original onto a substrate, and a sensor configured to detect light emerging from the projection optical system, the sensor including a light receiving element having a light receiving surface, and an optical member having a reflection surface which reflects the light emerging from the projection optical system toward the light receiving surface, wherein the reflection surface forms an acute angle with respect to the light receiving surface.

4 Claims, 8 Drawing Sheets

EXPOSURE APPARATUS AND DEVICE FABRICATION METHOD

BACKGROUND OF THE INVENTION

1. Field of the Invention

The present invention relates to an exposure apparatus and a device fabrication method.

2. Description of the Related Art

An exposure apparatus which projects and transfers a circuit pattern formed on a mask (reticle) onto a substrate such as a wafer via a projection optical system has conventionally been employed to fabricate a fine semiconductor device or a liquid crystal display device such as a semiconductor memory or logic circuit. The minimum dimension (resolution) of a pattern which can be transferred by the exposure apparatus is proportional to the exposure light wavelength, while it is inversely proportional to the numerical aperture (NA) of the projection optical system. In view of this, the shorter the wavelength and the higher the NA, the better the resolution. Along with the recent demand for micropatterning semiconductor devices, higher resolutions are becoming necessary.

Immersion exposure is receiving a great deal of attention as a technique of increasing the NA of the projection optical system. The immersion exposure further increases the NA of the projection optical system by using a liquid as a medium that fills the space under the projection optical system on the wafer side (image plane side). The numerical aperture NA of the projection optical system is given by NA=n·sin θ where n is the refractive index of the medium that fills the space under the projection optical system on the wafer side. A conventional exposure apparatus in which the space between a projection optical system and a wafer is filled with air (n=1) has an NA of 1 as a limit value. To improve this situation, the space between the projection optical system and the wafer is filled with a medium (liquid) having a refractive index higher than that of air so as to increase the NA of the projection optical system to that matching the refractive index of the medium. This makes it possible to provide exposure apparatuses which meet an increasingly growing demand for improving the resolution.

The control of an exposure apparatus requires monitoring various physical quantities to manage the apparatus state. For example, the exposure light quantity and imaging position are measured by monitoring actual exposure light having passed through a projection optical system, and are used to control the apparatus. Therefore, a light quantity sensor is required to have the capability to monitor physical quantities in an immersed state, that is, at a maximum NA.

The exposure apparatus uses, as the light quantity sensor, a photoelectric conversion device such as a photodiode which converts a light quantity into an electrical signal. In general, a photodiode is relatively susceptible to humidity. To prevent an immersion material from entering the photodiode, it is necessary to block the immersion material by inserting a transmission substrate on the image plane side of the projection optical system.

However, as the transmission substrate is inserted on the image plane side of the projection optical system, the light quantity sensor receives exposure light having passed through the projection optical system via the transmission substrate. In this case, light having an NA that exceeds 1 cannot reach the light receiving surface because it is totally reflected by the exit surface of the transmission substrate. To solve this problem, there is proposed a technique of preventing light having an NA that exceeds 1 from being totally reflected by the exit surface of the transmission substrate by bringing the transmission substrate into optical contact with a planoconvex lens. There are also proposed techniques of preventing light having an NA that exceeds 1 from being totally reflected by the exit surface of the transmission substrate in the following way. That is, the exit surface of the transmission substrate is designed as a diffusing surface, light is guided to the light receiving surface by reflecting it on the side surface of a cylindrical prism, or an optical fiber is used. Patent references are Japanese Patent Laid-Open Nos. 2005-268744, 2005-175034, and 2005-223275.

Unfortunately, the prior arts pose the following problems.

In the conventional technique of condensing light using a planoconvex lens, a measurement error due to the angle characteristic of the light receiving element is relatively large because the light emerging from the transmission substrate enters the light receiving surface while maintaining almost the same angle as the exit angle with respect to the transmission substrate. To solve this problem, the incident angle of the light with respect to the light receiving surface may be decreased by further inserting a plurality of lenses into the subsequent stage of the planoconvex lens. This, however, increases the number of lenses, resulting in a complex structure. When the angle of the light emerging from the planoconvex lens is relatively large, the area of the light receiving surface (light receiving element) of the light quantity sensor must be increased. This makes it difficult to ensure a space for accommodating the light quantity sensor and manufacture it. It is also possible to decrease the distance between the transmission substrate and the light quantity sensor so as not to increase the area of the light receiving surface. However, in an illumination mode in which a coherent factor σ of an illumination system is low (low σ), the incidence area of the light receiving element is narrowed down so that energy is concentrated on a specific portion, leading to a poor durability of the light quantity sensor.

In the conventional technique of guiding light to the light receiving surface by reflecting it on the side surface of a cylindrical prism, the light reaches the exit surface of the cylindrical prism while maintaining the same NA as that with which it enters the prism. For this reason, high-NA light is totally reflected by the exit surface of the prism without being transmitted through it. To solve this problem, the exit surface of the cylindrical prism may be brought into optical contact with the light receiving element, or the cylindrical prism may have a curved exit surface. However, these arrangements pose the following problems.

The arrangement in which the exit surface of the cylindrical prism is brought into optical contact with the light receiving element is impractical because they are likely to separate from each other. This is because a cylindrical prism and light receiving element are generally made of different materials, which come into optical contact with each other with a relatively weak bonding strength. The arrangement in which the cylindrical prism has a curved exit surface is also impractical because the light emerges from the prism and enters the light receiving surface while maintaining almost the same NA as that with which it enters the prism. This poses problems that a measurement error due to the angle characteristic of the light receiving element increases, or that the size of the light receiving element of the light quantity sensor must be increased.

The conventional techniques of designing the exit surface of the transmission substrate as a diffusing surface and using an optical fiber result in difficulty in manufacturing an optical element and in a complex structure.

SUMMARY OF THE INVENTION

The present invention provides an exposure apparatus having a light quantity sensor (light detection sensor) that is advantageous to increasing the NA of exposure light.

According to one aspect of the present invention, there is provided an exposure apparatus comprising a projection optical system configured to project a pattern image of an original onto a substrate, and a sensor configured to detect light emerging from the projection optical system, the sensor including a light receiving element having a light receiving surface, and an optical member having a reflection surface which reflects the light emerging from the projection optical system toward the light receiving surface, wherein the reflection surface forms an acute angle with respect to the light receiving surface.

According to another aspect of the present invention, there is provided a device fabrication method comprising steps of exposing a substrate using the above exposure apparatus, and performing a development process for the substrate exposed.

Further features of the present invention will become apparent from the following description of exemplary embodiments with reference to the attached drawings.

DESCRIPTION OF THE EMBODIMENTS

An embodiment of the present invention will be described in detail below with reference to the accompanying drawings.

Figure 1:
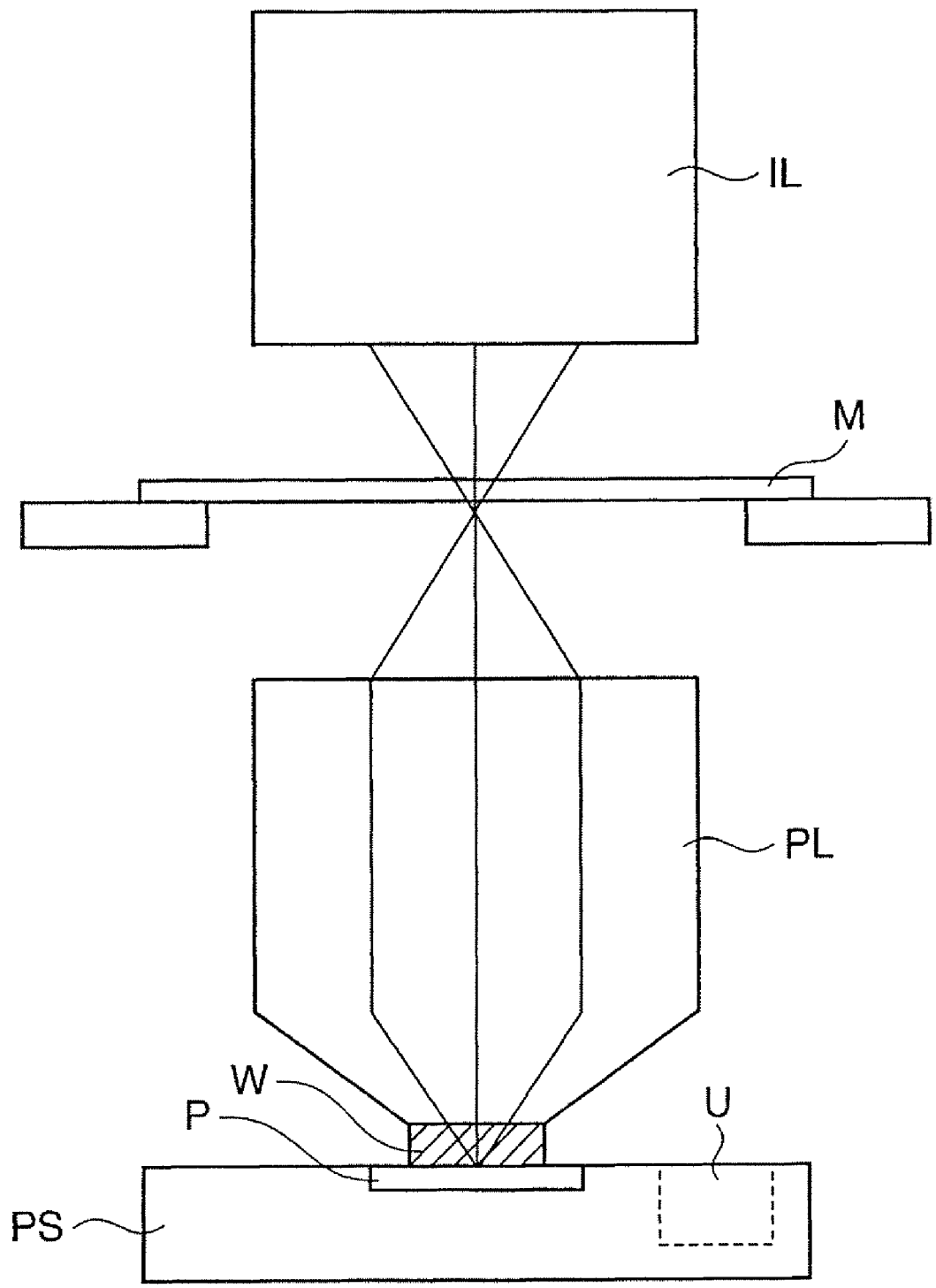
FIG. 1 is a schematic view of an immersion exposure apparatus according to one aspect of the present invention.

FIG. 1 is a schematic view showing an embodiment using an immersion exposure apparatus. The immersion exposure apparatus according to this embodiment includes an illumination optical system IL for guiding a light beam emitted by a light source to a mask (original) M, and a projection optical system PL for projecting the pattern image of the mask M onto a substrate P coated with a photosensitive material. The immersion exposure apparatus according to this embodiment achieves an increase in NA by filling the space between the lower end surface of the projection optical system PL and the surface of the substrate P with a liquid (immersion material) W and performing exposure. A light quantity sensor U is accommodated in a substrate stage PS to be flush with the substrate P. The light quantity sensor U is a sensor for detecting the light emerging from the projection optical system PL. The light quantity sensor U is used to, for example, measure the exposure light quantity distribution on the image plane of the projection optical system PL.

Figure 2:
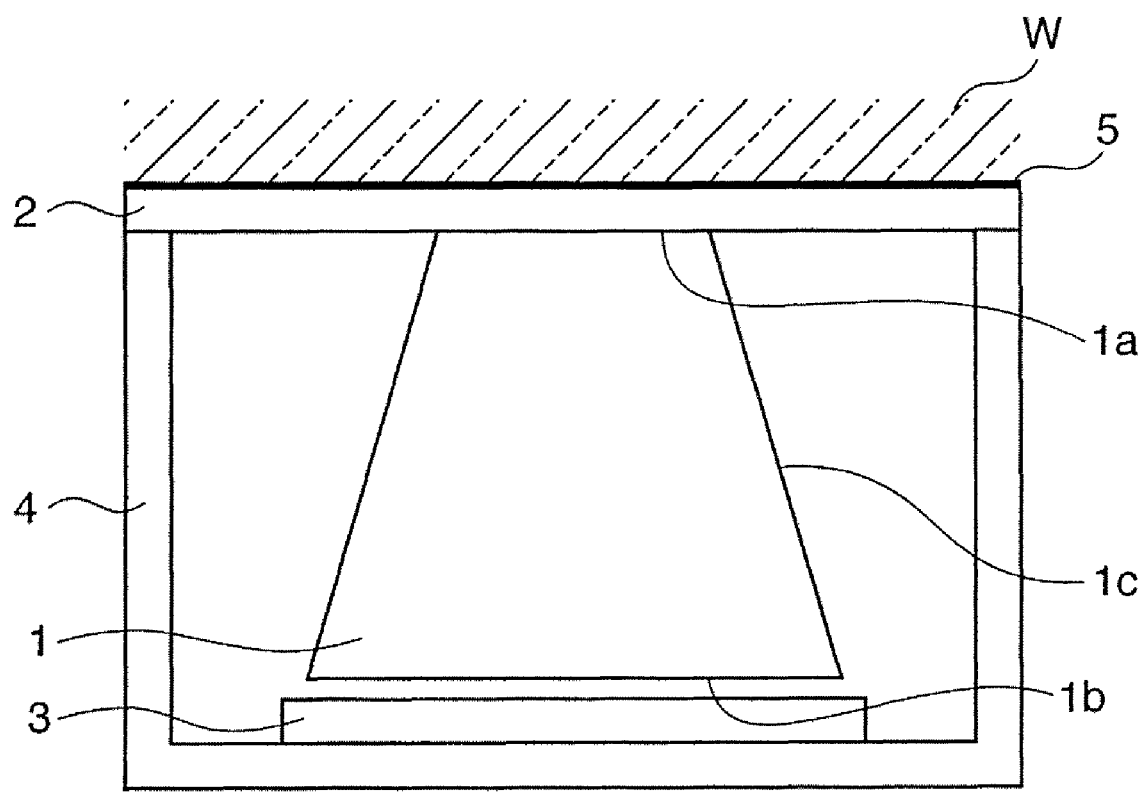
FIG. 2 is a view for explaining a light quantity sensor of the immersion exposure apparatus shown in FIG. 1.

FIG. 2 is a schematic view showing the light quantity sensor U. Reference numeral 1 denotes a circular truncated conical prism (truncated conical prism), reference numeral 2 denotes a transmission substrate, reference numeral 3 denotes a light receiving element, reference numeral 4 denotes a holding structure, and reference numeral 5 denotes a light shielding film on which a pattern 6 with an opening is formed. The immersion material W uses a liquid such as pure water.

The truncated conical prism 1 is made of, for example, quartz, and deflects high-NA light on its side surface (reflection surface) using total reflection by the difference in refractive index between the truncated conical prism 1 and its ambient gas (air). Reference numeral 1a indicates the upper surface of the truncated conical prism 1 on the side of the immersion material W, reference numeral 1b indicates the lower surface of the truncated conical prism 1 on the side of the light receiving element 3, and reference numeral 1c indicates the side surface of the truncated conical prism 1. The side surface 1c of the truncated conical prism 1 forms acute angles with respect to the transmission substrate and the light receiving surface of the light receiving element 3. The side surface 1c of the truncated conical prism 1 is provided between the pattern 6 and the light receiving element 3, and functions as a reflection surface which reflects light having passed through the opening toward the light receiving element 3. With this arrangement, the side surface 1c of the truncated conical prism 1 totally reflects even high-NA light having passed through the opening to decrease its incident angle with respect to the lower surface 1b of the truncated conical prism 1. Then, the light can enter the light receiving element 3 upon being transmitted through the lower surface 1b.

The transmission substrate 2 is arranged such that its surface coated with the light shielding film 5 comes into contact with the immersion material. The truncated conical prism 1 is arranged such that the lower surface 1b having a larger sectional diameter faces the light receiving element 3. The upper surface 1a of the truncated conical prism 1, which has a smaller sectional diameter, is in optical contact with a surface of the transmission substrate 2, which is coated with no light shielding film. These surfaces are brought into optical contact with each other by taking account of a case wherein the exposure light uses ArF excimer laser light having a wavelength of 193 nm, against which an adhesive generally has a poor durability. In view of this, the truncated conical prism 1 and transmission substrate 2 are desirably made of the same material.

The transmission substrate 2 is coated with the light shielding film 5, and is patterned to have a pattern 6 with an opening such as a pinhole pattern or line-and-space pattern in accordance with the performance of an exposure apparatus to be measured. The pattern surface of the transmission substrate 2 may be coated with a water repellent coating.

The transmission substrate 2 is desirably a plane-parallel plate having a diameter larger than that of the truncated conical prism 1. The reason is as follows. If the diameter of the transmission substrate 2 is smaller than that of the truncated conical prism 1, the holding structure 4 for holding the transmission substrate 2 or truncated conical prism 1 immediately above the light receiving element 3 is necessary. In this arrangement, the immersion material may leak out from the gap between the truncated conical prism 1 and the holding structure 4, so the light receiving element 3 may get wet. This makes it necessary to hold the transmission substrate 2 or truncated conical prism 1 at a position sufficiently spaced apart from the light receiving element 3. The diameter of the transmission substrate 2 is desirably larger than that of the truncated conical prism 1. Another reason is attributed to a problem in terms of the manufacture. As described above, the light shielding film 5 is patterned to have various openings in accordance with the performance of an exposure apparatus to be measured. The light shielding film 5 is sometimes patterned to have an opening on the order of several nm. In order to pattern the light shielding film 5 to have such a fine opening, a plane-parallel plate having a predetermined diameter larger than that of the prism is more suitable for easy manufacture than a substrate surface having a diameter smaller than that of the prism.

The light receiving element 3 includes a photoelectric conversion device such as a photodiode which converts a light quantity to an electrical signal. In general, a photoelectric conversion device has an angle characteristic in which the larger the light incident angle, the smaller the output value.

Figure 6:
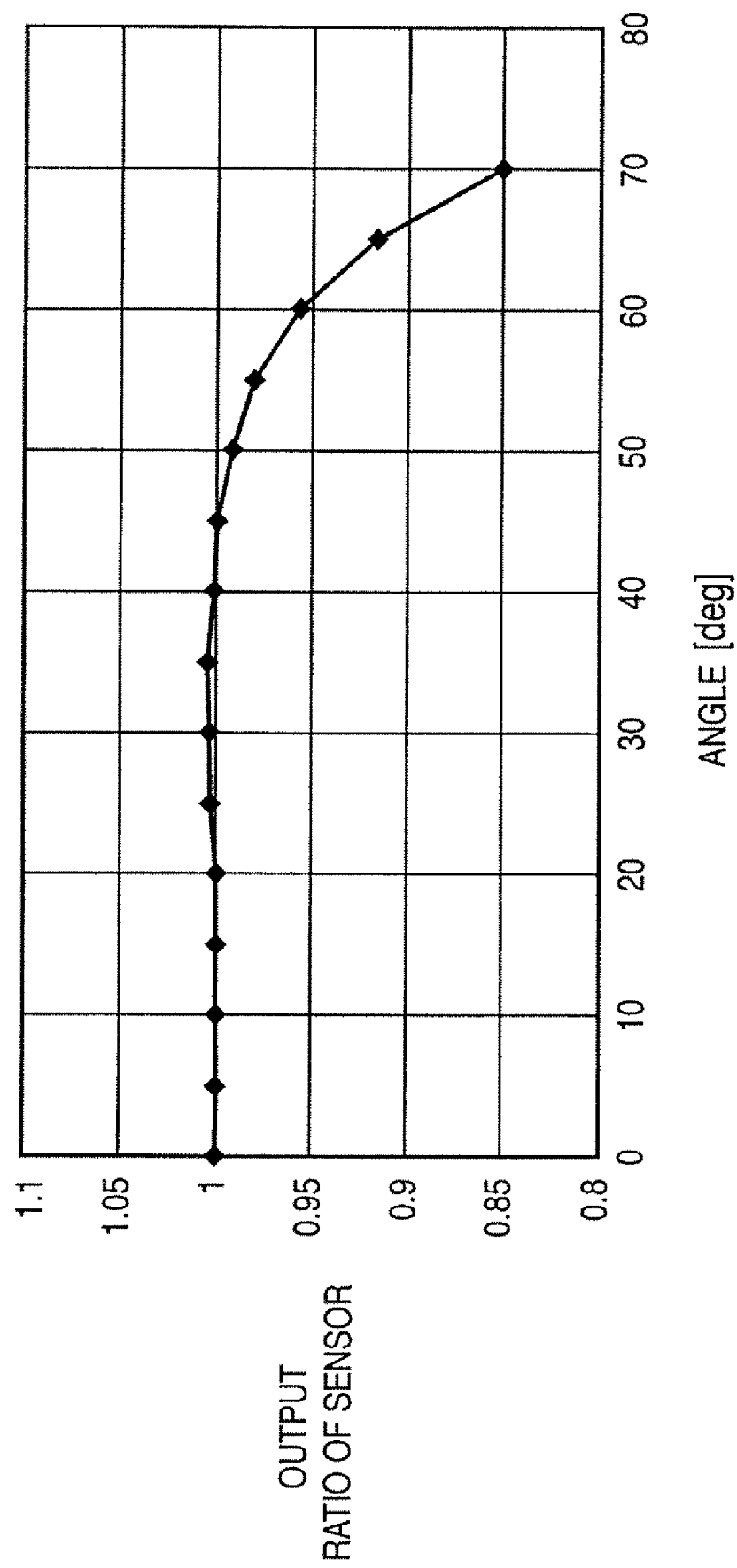
FIG. 6 is a graph showing the incident angle characteristic of a light receiving element of the light quantity sensor shown in FIG. 2.

FIG. 6 is a graph showing the incident angle characteristic of the light receiving element 3 used in this embodiment. The abscissa indicates the light incident angle with respect to the light receiving element, and the ordinate indicates the output ratio of the sensor. FIG. 6 reveals that when the light incident angle with respect to the light receiving element 3 falls within 45°, the output from the sensor is less likely to change even when the incident angle changes.

Figure 3:
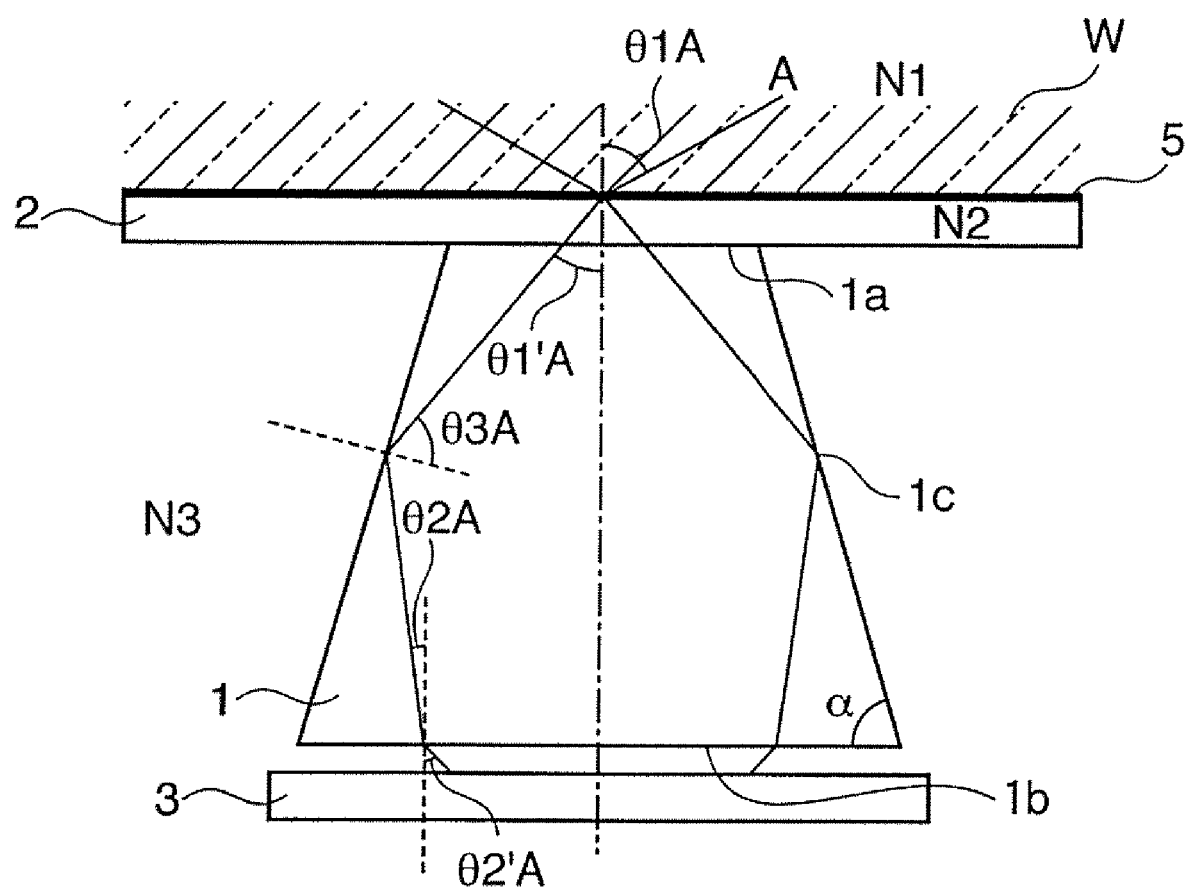
FIG. 3 is a view for explaining a preferable shape of a truncated conical prism of the light quantity sensor shown in FIG. 2.

The optimal value of an inclination angle α of the side surface 1c of the truncated conical prism 1 will be explained with reference to FIG. 3. FIG. 3 shows a light beam A with a maximum NA to be captured in the light receiving element 3. The incident angles, transmission angles, and the like of the light beam A are expressed as follows. That is, let θ1A be the angle at which the light beam having passed through the immersion material W enters the transmission substrate 2; θ1'A, the angle at which the light beam is transmitted through the transmission substrate 2; θ2A, the angle at which the light beam enters the lower surface (exit surface) 1b of the truncated conical prism 1; θ2'A, the angle (the incident angle with respect to the light receiving surface) at which the light beam is transmitted through the lower surface 1b of the truncated conical prism 1; θ3A, the angle at which the light beam enters the side surface 1c of the truncated conical prism 1; α, the inclination angle of the side surface 1c of the truncated conical prism 1; N1, the refractive index of the immersion material W; N2, the refractive indices of the transmission substrate 2 and truncated conical prism 1; and N3, the refractive index of the ambient gas of the truncated conical prism 1. Then, we have relational expressions between the above-described angles:

$$N1 \times \sin\theta 1A = N2 \times \sin\theta 1'A \quad (1)$$

$$N2 \times \sin\theta 2A = N3 \times \sin\theta 2'A \quad (2)$$

$$\theta 3A = 180 - \theta 1'A - \alpha \quad (3)$$

$$\theta 2A = 2 \times \alpha + \theta 1'A - 180 \quad (4)$$

Note that the transmission substrate 2 and truncated conical prism 1 are made of the same material.

Assuming here that the exposure light is ArF excimer laser light having a wavelength of 193 nm, the immersion material W is pure water, the glass materials of the transmission substrate 2 and truncated conical prism 1 are quartz, and the ambient gas of the truncated conical prism 1 is air, N1=1.44, N2=1.56, and N3=1. In this case, a condition under which the light beam is totally reflected at the boundary between the quartz and the air is a critical angle θc=39.9° or more.

If the light beam has an NA=1, the angle θ1'A at which it is transmitted through the transmission substrate 2 is calculated as 39.9° from equation (1). When the side surface 1c of the truncated conical prism 1 is not inclined (α=90°), we have θ3A=50.1° from equation (3). Since the critical angle in this case is θc=39.9° or more, that is, satisfies the total reflection condition, the light beam having an NA=1 is totally reflected by the side surface 1c of the truncated conical prism 1. Since we have θ2A =39.9° from equation (4), the light beam is totally reflected by the lower surface 1b of the truncated conical prism 1 and cannot emerge from the truncated conical prism 1. This reveals that in order to guide a light beam having an NA of 1 or more to emerge from the truncated conical prism 1, the side surface 1c of the truncated conical prism 1 needs to be inclined with respect to the normal to the light receiving surface of the light receiving element 3. That is, it is necessary that α<90° and the side surface 1c of the truncated conical prism 1 forms an acute angle with respect to the transmission substrate 2 or the light receiving surface of the light receiving element 3.

Assume the use of a light receiving element 3 having an incident angle characteristic which does not practically produce any measurement error by setting the light incident angle θ2'A with respect to the light receiving element 3 to fall within 45°. In this case, the calculation of equations (2) and (4) reveals that a need only be 83° or less.

If the light beam has an NA=1.3, the angle θ1'A at which it is transmitted through the transmission substrate 2 is calculated as 56.4°. The calculation of equations (2) and (4) reveals that in order to set the light incident angle θ2'A with respect to the light receiving element 3 to fall within 45°, α needs to be 75° or less.

In this way, the inclination angle α of the side surface 1c of the truncated conical prism 1 can be determined from the NA of a light beam to be measured and the incident angle characteristic of the light receiving element 3.

Figure 4:
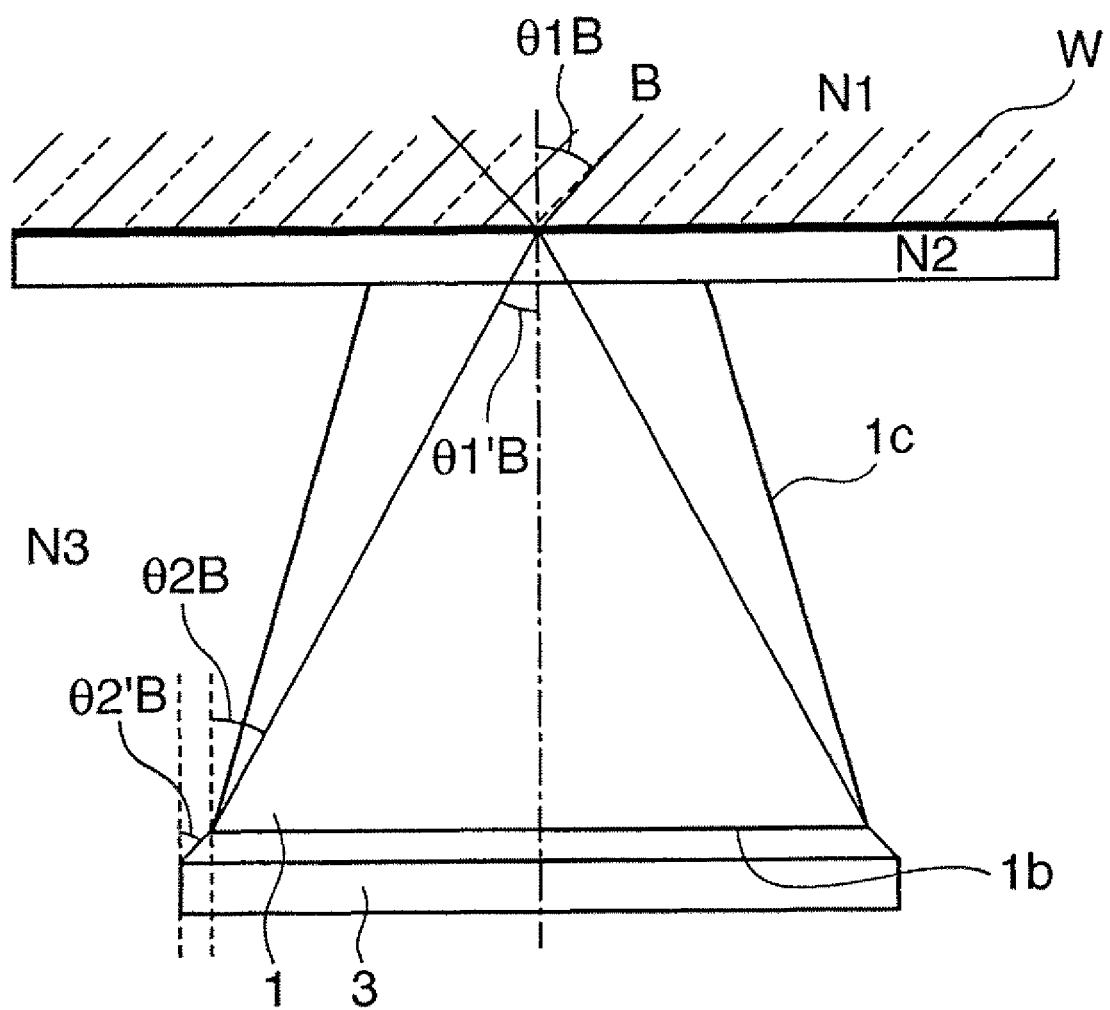
FIG. 4 is a view for explaining a preferable arrangement of the light quantity sensor shown in FIG. 2.

The NA of a light beam required to be totally reflected by the side surface 1c of the truncated conical prism 1 will be explained with reference to FIG. 4. In the arrangement shown in FIG. 4, light beams are condensed in the light receiving element 3. A light beam which enters the light receiving element 3 at a maximum incident angle is a light beam B which passes through the edge of the lower surface 1b of the truncated conical prism 1.

When the transmission substrate 2 and truncated conical prism 1 are made of the same glass material, the angle at which the light beam B is transmitted through the transmission substrate 2 is equal to the angle at which the light beam B enters the lower surface 1b of the truncated conical prism 1 (θ1'B=θ2B). From equations (1) and (2), the NA at which the light beam enters the substrate is given by:

$$NA = N1 \times \sin\theta 1B = N3 \times \sin\theta 2'B \quad (5)$$

To reduce the maximum incident angle θ2'B with respect to the light receiving element 3 to a certain value, a light beam having an NA equal to or higher than that calculated from equation (5) needs to be totally reflected by the side surface 1c of the truncated conical prism 1.

Consider, for example, a case wherein the exposure light is ArF excimer laser light having a wavelength of 193 nm, the immersion material W is pure water, the glass materials of the transmission substrate 2 and truncated conical prism 1 are quartz, and the ambient gas of the light receiving element 3 is air. Equation (5) reveals that in order to set the light incident angle with respect to the light receiving element 3 to fall within 45°, a light beam having an NA of 0.7 or more when entering the substrate needs to be totally reflected by the side surface 1c of the truncated conical prism 1.

An arrangement (FIG. 5A) using a truncated conical prism as a deflecting optical element, an arrangement (FIG. 5B) using a planoconvex lens, and a case wherein the distance between the transmission substrate 2 and the light receiving element 3 is decreased will be explained with reference to FIGS. 5A to 5C.

Figure 5:
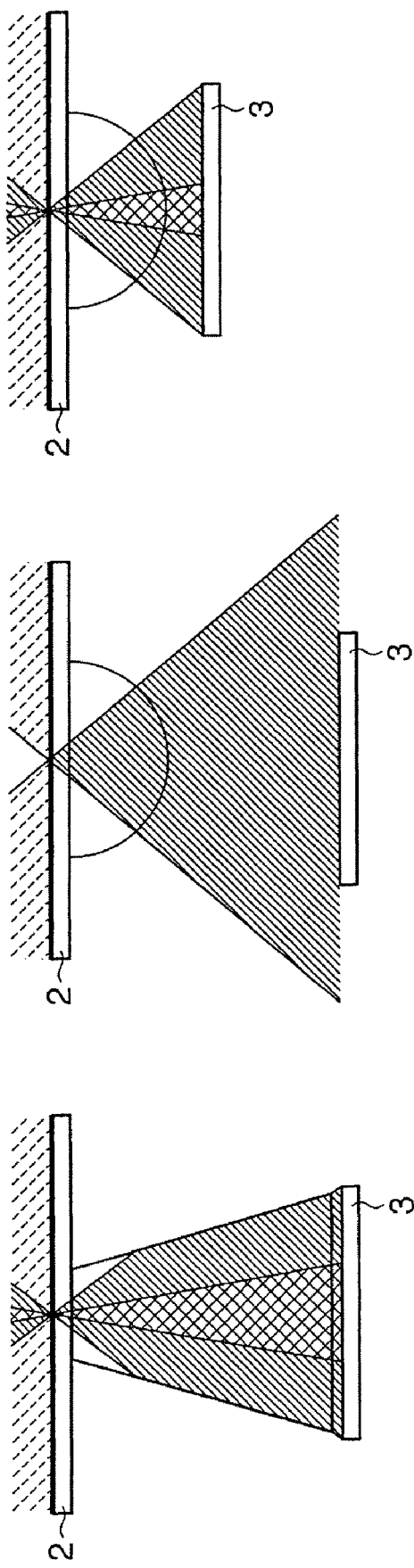
FIGS. 5A to 5C are views for comparing an arrangement using a truncated conical prism as a deflecting optical element and an arrangement using a planoconvex lens.

As shown in FIG. 5B, in the arrangement using a planoconvex as a deflecting optical element, a light beam enters the light receiving element 3 while maintaining almost the same angle as that at which it emerges from the transmission substrate 2. For this reason, a light beam having a higher NA enters the light receiving element 3 at a larger angle, resulting in an increase in the incident angle characteristic of the light receiving element 3. In addition, the effective region of the light receiving element 3 needs to be widened because the light beam greatly diverges on the surface of the light receiving element 3.

As shown in FIG. 5C, the distance between the transmission substrate 2 and the light receiving element 3 may be decreased so as not to widen the effective region of the light receiving element 3. However, if σ is low, the light irradiation region on the light receiving surface of the light receiving element 3 narrows and therefore the energy density increases, leading to a poor durability of the light receiving element 3.

As shown in FIG. 5A, in the arrangement using a truncated conical prism as a deflecting optical element, a high-NA light beam is totally reflected by the side surface 1c of the truncated conical prism 1, as described above. This decreases the angle at which even a high-NA light beam enters the light receiving element 3. It is also possible to condense light beams in a predetermined effective region of the light receiving element 3. Since the transmission substrate 2 and light receiving element 3 can be separated from each other by a predetermined distance so that the incidence area of the light receiving element 3 remains almost the same even though σ changes, the durability of the light receiving element 3 never lowers even when σ is low.

A truncated conical prism has been exemplified as an optical member which totally reflects a light beam on its side surface. However, the optical member is not limited to a truncated conical prism and may be a truncated pyramidal prism or a prism having a paraboloidal curved side surface. In addition, a light beam need not always enter the side surface (reflection surface) at an incident angle equal to or larger than a critical angle which allows total reflection, and may be reflected using, for example, a mirror as the reflection surface instead of using total reflection. Although this embodiment has exemplified an immersion exposure apparatus, the exposure apparatus used is not particularly limited to it. It is also possible to adopt a so-called dry exposure apparatus in which the space between a projection optical system and a substrate is not filled with a liquid. In dry exposure, measurement can be performed without using the transmission substrate 2.

As described above, a truncated conical, truncated pyramidal, or paraboloidal reflection surface, for example, need not form a right angle but forms an acute angle with respect to the light receiving surface (including a plane parallel to the light receiving surface) of a light receiving element.

Figure 7:
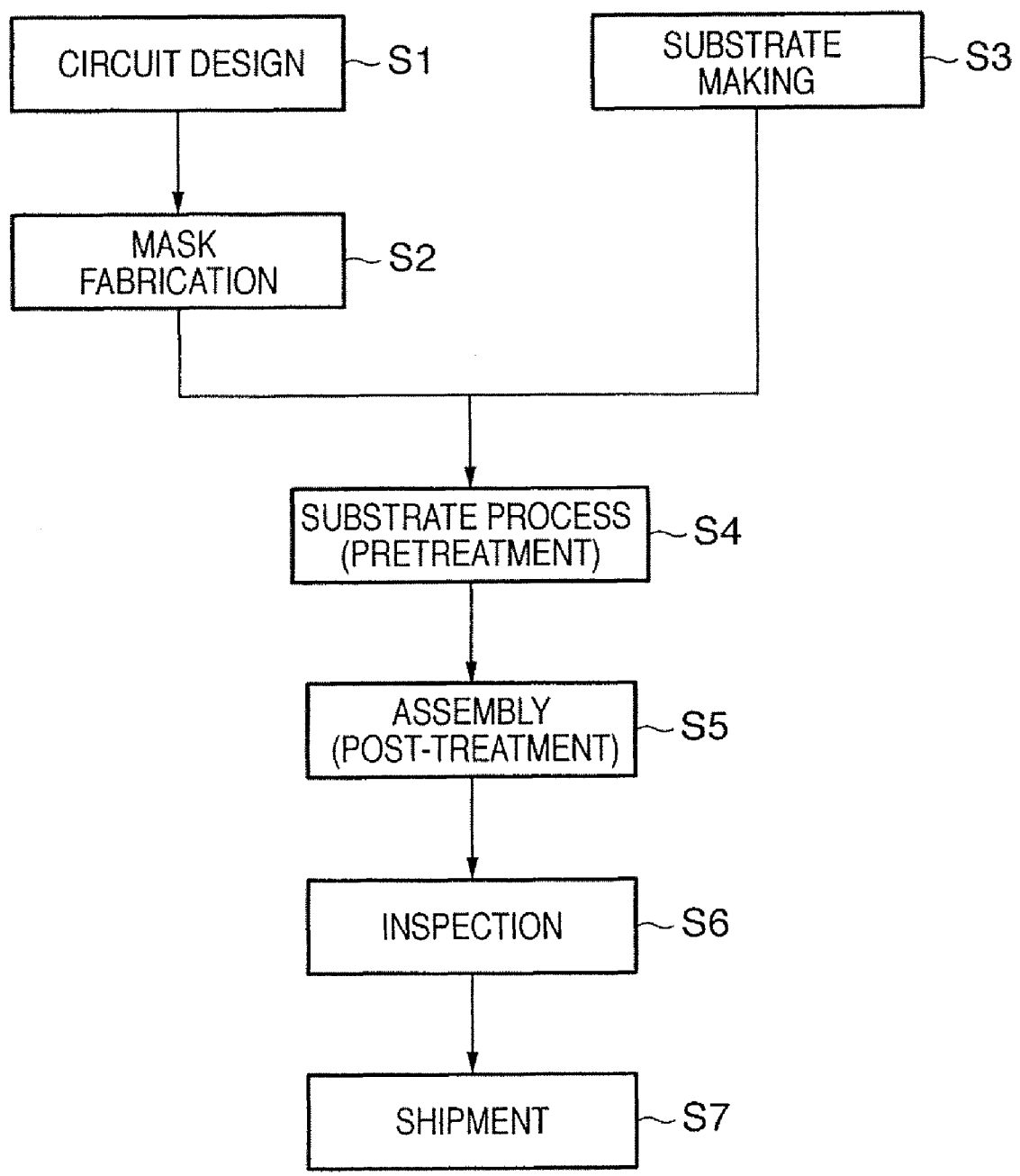
FIG. 7 is a flowchart for explaining a method for fabricating devices.
Figure 8:
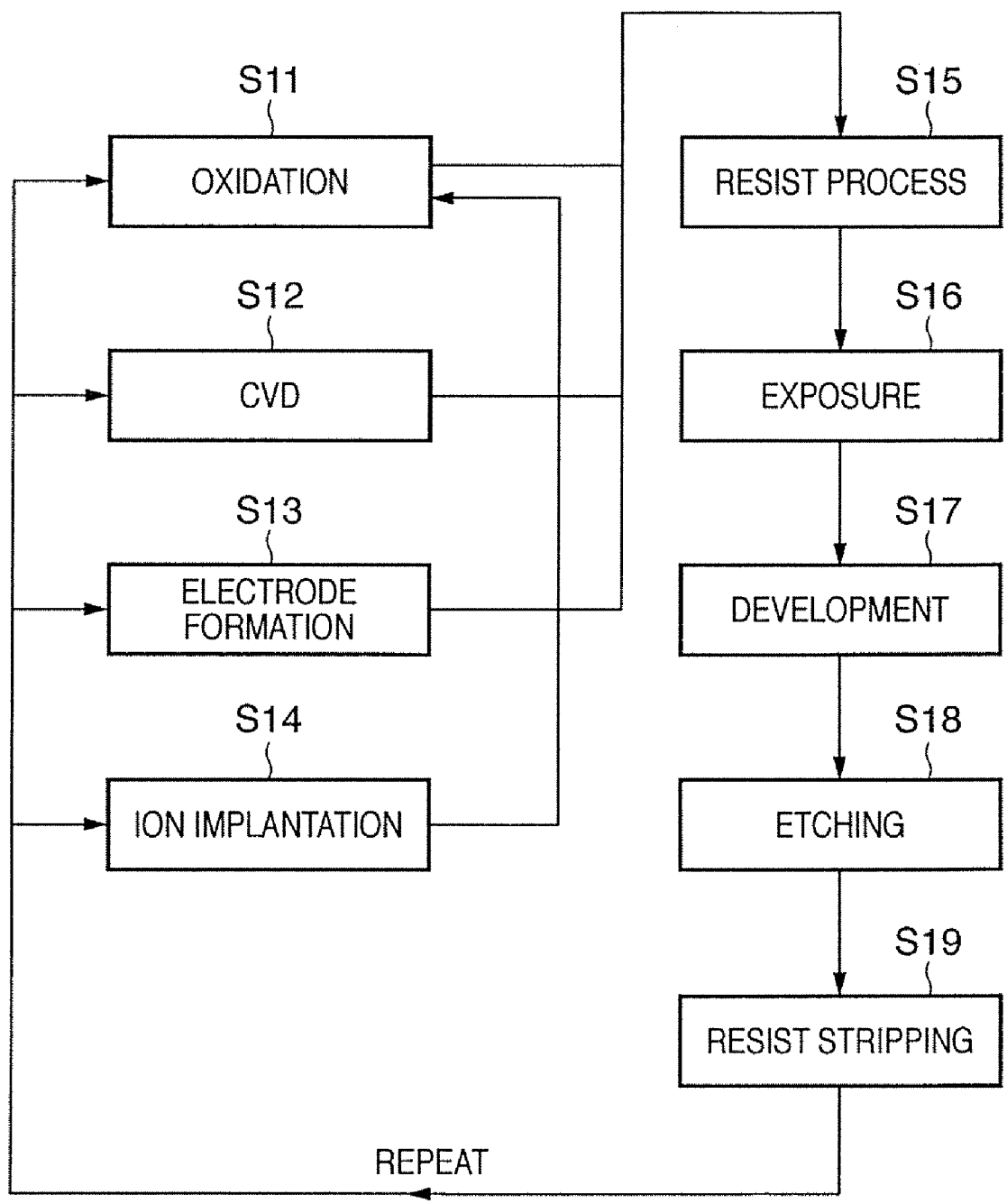
FIG. 8 is a detail flowchart of a wafer process in Step 4 of FIG. 7.

Referring now to FIGS. 7 and 8, a description will be given of an embodiment of a device fabrication method using the above mentioned exposure apparatus. FIG. 7 is a flowchart for explaining how to fabricate devices (i.e., semiconductor chips such as IC and LSI, LCDs, CCDs, and the like). Here, a description will be given of the fabrication of a semiconductor chip as an example. Step 1 (circuit design) designs a semiconductor device circuit. Step 2 (mask fabrication) forms a mask having a designed circuit pattern. Step 3 (substrate making) manufactures a substrate using materials such as silicon. Step 4 (substrate process), which is also referred to as a pretreatment, forms the actual circuitry on the substrate through lithography using the mask and substrate. Step 5 (assembly), which is also referred to as a post-treatment, forms into a semiconductor chip the substrate formed in Step 4 and includes an assembly step (e.g., dicing, bonding), a packaging step (chip sealing), and the like. Step 6 (inspection) performs various tests on the semiconductor device made in Step 5, such as a validity test and a durability test. Through these steps, a semiconductor device is finished and shipped (Step 7).

FIG. 8 is a detailed flowchart of the wafer process in Step 4. Step 11 (oxidation) oxidizes the substrate's surface. Step 12 (CVD) forms an insulating layer on the substrate's surface. Step 13 (electrode formation) forms electrodes on the substrate by vapor disposition and the like. Step 14 (ion implantation) implants ions into the substrate. Step 15 (resist process) applies a photosensitive material onto the substrate. Step 16 (exposure) uses the above exposure apparatus to expose a circuit pattern from the mask onto the substrate. Step 17 (development) develops the exposed substrate. Step 18 (etching) etches parts other than a developed resist image. Step 19 (resist stripping) removes unused resist after etching. These steps are repeated to form multi-layer circuit patterns on the substrate. The device fabrication method of this embodiment may manufacture higher quality devices than the conventional one. Thus, the device fabrication method using the above exposure apparatus, and resultant devices constitute one aspect of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese application No. 2006-344694 filed on Dec. 21, 2006, which is hereby incorporated by reference herein in its entirely.

What is claimed is:

1. An exposure apparatus comprising:
a projection optical system configured to project a pattern image of an original onto a substrate; and
a sensor configured to detect light emerging from said projection optical system, said sensor including a light receiving element having a light receiving surface, and an optical member having a reflection surface which reflects the light emerging from said projection optical system toward said light receiving surface,
wherein said reflection surface forms an acute angle with respect to said light receiving surface,
wherein said reflection surface includes a side surface of a truncated conical shape or a truncated pyramidal shape,
wherein the optical member and the light receiving element are separated from each other, and
wherein a surface of a side of the light receiving element of the optical member is a plane.

2. The apparatus according to claim 1, wherein said light receiving surface forms an angle of not more than 83° with respect to said reflection surface.

3. The apparatus according to claim 1, wherein an incident angle at which the light enters said reflection surface is not less than a critical angle.

4. A device fabrication method comprising steps of:

exposing a substrate using an exposure apparatus; and performing a development process for the substrate exposed;

wherein the exposing apparatus includes a projection optical system configured to project a pattern image of an original onto a substrate, and a sensor configured to detect light emerging from said projection optical system, said sensor including a light receiving element having a light receiving surface, and an optical member having a reflection surface which reflects the light emerging from said projection optical system toward said light receiving surface;

wherein said reflection surface forms an acute angle with respect to said light receiving surface;

wherein said reflection surface includes a side surface of a truncated conical shape or a truncated pyramidal shape;

wherein the optical member and the light receiving element are separated from each other; and wherein a surface of a side of the light receiving element of the optical member is a plane.

* * * * *